United States Patent [19]

De Steur

[11] 4,301,413

[45] Nov. 17, 1981

[54] CIRCUIT ARRANGEMENT FOR AMPEROMETRIC TITRATION

[75] Inventor: Hubert De Steur, Drongen, Belgium

[73] Assignee: Siemens Aktiengesellschaft, Berlin & Munich, Fed. Rep. of Germany

[21] Appl. No.: 121,378

[22] Filed: Feb. 14, 1980

[30] Foreign Application Priority Data

Mar. 21, 1979 [DE] Fed. Rep. of Germany ....... 2911151

[51] Int. Cl.³ ............................................. G01N 27/42
[52] U.S. Cl. .................................................... 324/438
[58] Field of Search .............. 324/425, 438; 23/230 R

[56] References Cited

U.S. PATENT DOCUMENTS

| | | | |
|---|---|---|---|
| 2,994,590 | 8/1961 | Brems | 324/438 |
| 3,131,348 | 4/1964 | Taylor et al. | 324/438 |
| 3,186,800 | 6/1965 | Strickler | 324/438 |
| 3,248,309 | 4/1966 | Robinson | 324/438 |

*Primary Examiner*—Michael J. Tokar

*Attorney, Agent, or Firm*—Hill, Van Santen, Steadman, Chiara & Simpson

[57] ABSTRACT

A circuit arrangement is disclosed for determining the end point in an amperometric titration, in which the current between a working electrode and a counter electrode is measured as a function of the total volume of the titration agent added in volume units. The working electrode is operated with a constant polarization voltage with respect to a reference electrode and a closed-loop control is provided for holding the polarization voltage prescribed between the working electrode and the reference electrode at a constant. The prescribed rated value voltage is compared to the actual value voltage identified between the working electrode and the reference electrodes. The reference value voltage is prescribed with the assistance of a reference value generator, the actual value voltage is identified in a high resistance manner with the assistance of an impedance transformer and the reference value/actual value deviation is compensated by way of a summing integrator.

8 Claims, 3 Drawing Figures

4,301,413

CIRCUIT ARRANGEMENT FOR AMPEROMETRIC TITRATION

BACKGROUND OF THE INVENTION

1. Field of the Invention

The present invention relates to a circuit arrangement for an amperometric titration for determining the end point, in which the current between a working electrode and a counter electrode is measured as a function of the total volume of the titration agent added in volume units, and in particular to a circuit arrangement in which the working electrode is operated with a constant polarization voltage with respect to a reference electrode and a closed-loop control is provided for holding the polarization voltage prescribed between the working and the reference electrodes constant, whereby a prescribed reference value voltage is compared to the actual value voltage identified between the working and reference electrodes.

2. Description of the Prior Art

A measurement circuit operating according to the above principle is set forth, for example, in the book "Grundlagen der Technischen Elektrochemie" by Heitz/Kreysa, Verlag Chemie Weinheim/New York, 1971, pp. 6-7. In that arrangement, a constant potential with respect to a reference electrode is applied by means of an electronic potentiostat to the working electrode and the current is measured with the assistance of a milliammeter. By way of a closed-loop control, the current is controlled in such a manner that the difference between a prescribed reference value voltage and the potential between the working and reference electrodes becomes a minimum. This known measurement circuit not only does not operate with precision sufficient for a titration, but is also not suitable for the automation of an amperometric titration for determining the end point, since it is not in a position to emit a magnitude proportional to the current.

SUMMARY OF THE INVENTION

The object of the present invention is to provide a circuit arrangement of the type generally mentioned above which operates with sufficient accuracy for providing an amperometric titration and which can be combined, without further effort, with an automatic evaluation method for determining the end point of the titration.

The above object is achieved, according to the present invention, in that the reference value voltage is prescribed with the assistance of a reference value generator, the actual value voltage is identified in a high-resistance manner with the assistance of an impedance transformer, and the reference value/actual value deviation is compensated by way of a summing integrator. Preferably, the reference value generator comprises a voltage divider stabilized with a Zener diode. By doing so, one has the possibility that the reference value voltage can be easily adapted to the respective conditions, whereby it is guaranteed that the voltage between the working electrode and the reference electrode is held sufficiently constant during the amperometric titration.

The output voltage of the summing integrator is applied to the counter electrode by way of a resistor which serves as a voltage transformer, whereby the potentials occurring at the voltage transformer are measured in a high resistant manner and the potential difference is formed by means of a differentiator. This potential difference is exactly proportional to the current in the electrode measuring system. The output signal of the differentiator can be directly supplied to an evaluation device for determining the end point.

BRIEF DESCRIPTION OF THE DRAWINGS

Other objects, features and advantages of the invention, its organization, construction and operation will be best understood from the following detailed description, taken in conjuction with the accompanying drawings, on which.

DESCRIPTION OF THE PREFERRED EMBODIMENTS

Figure 1:
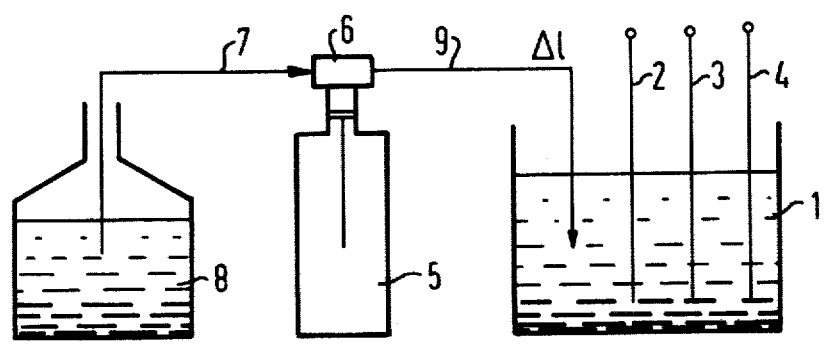
FIG. 1 is a schematic illustration of a basic arrangement for an amperometric titration.

In FIG. 1, a titration vessel 1 has a plurality of electrodes therein, including a working electrode 2, a reference electrode 3 and a counter electrode 4. With the assistance of a motorized piston burette 5, on which a controllable valve 6 is located, a suitable titration agent is dispensed from a container 8 by way of a line 7, through the valve 6, and delivered by way of a line 9 to the titration vessel 1 in volume units $\Delta 1$. As soon as this titration end point is determined, the motorized piston burette 5 is shut down.

In FIG. 1, therefore, only such parts are illustrated as are of significance for an amperometric titration and not, however, sample-taking, additional additives, particularly distilled water for dilution.

Figure 2:
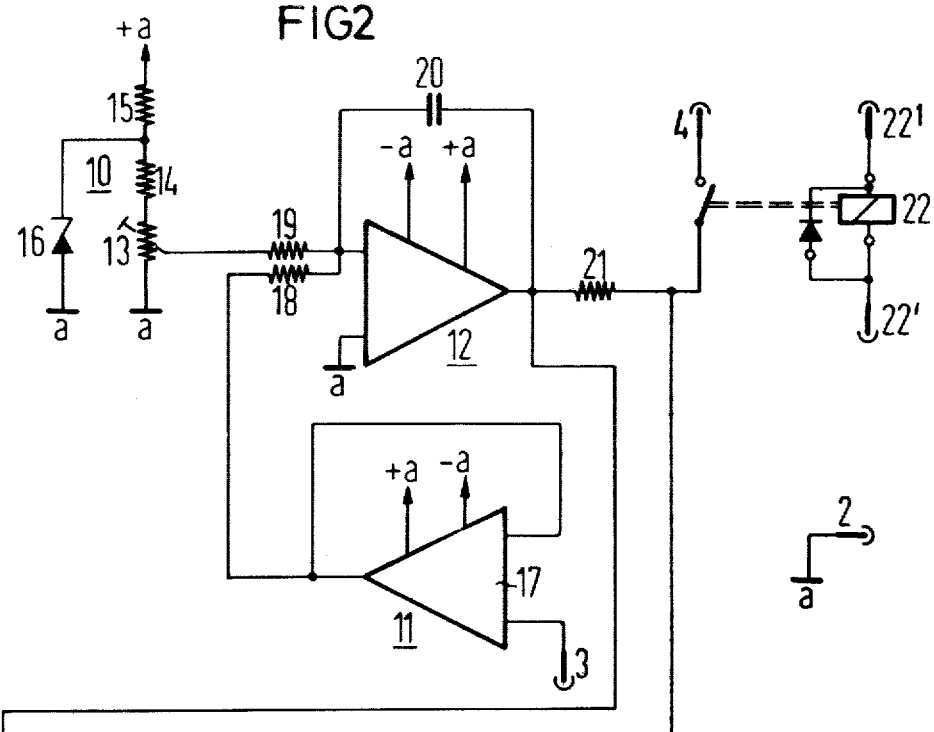
FIG. 2 is a schematic circuit diagram of an arrangement constructed in accordance with the present invention.

A circuit arrangement constructed in accordance with the present invention is illustrated in FIG. 2. The circuit comprises a closed-loop control which includes a reference value generator 10, an actual value generator 11 and a summing integrator 12. The reference value generator comprises a voltage divider having a plurality of resistors 13-15, the resistor 13 being adjustable for prescribing the reference value. For holding the voltage constant, a Zener diode 16 is connected in parallel to the resistors 13 and 14. As can be seen from the drawing, the working electrode 2 is connected to ground potential a, to which the Zener diode 16 and the resistor 13 are also connected. The reference value of the polarization voltage with respect to the reference electrode 3 is set with respect to the working electrode 2 (ground a) at the resistor 13, which is a low resistance.

The actual value of the polarization voltage is tapped at the reference electrode 3 in a high resistance manner with the assistance of an impedance transformer 17 and is applied by way of a resistor 18 to the inverting input of the summing integrator 12 which also receives the reference value voltage by way of a resistor 19. The non-inverting input of the summing integrator 12 is connected to ground a. The output of the summing integrator 12 is connected to the inverting input by way of a capacitor 20. By means of an appropriate dimensioning of the RC element consisting of the capacitor 20 and the resistors 18 and 19, the control dynamics can be adapted to every specific task. Every rated value/actual value deviation, therefore, is compensated by way of the summing integrator 12.

The output voltage of the summing integrator 12 is applied to the counter electrode 4 by way of a resistor 21 which serves as a voltage transformer, and by way of a switching contact of a relay 22. Normally, the switching contact of the relay 22 is closed. It is only opened during the titration pause in order to prevent undesired polarization phenomena at the counter-electrode 4 and at the working electrode 2. The voltage applied to the counter electrode 4 by way of the resistor 21 is dimensioned in such a manner that the potential difference between the reference electrode 3 and the working electrode 2 corresponds to the reference value voltage applied at the resistor 13. This voltage, therefore, influences the current between the working electrode 2 and the counter electrode 4. This current produces a voltage drop in the resistor 21. The potentials at the terminals of the resistor 21 are separately identified with the assistance of two impedance transformers 23 and 24 and are applied by way of a pair of resistors 25 and 26 to the inputs of a differentiator 27, with whose assistance these potentials are measured with respect to ground and the difference of these potentials is formed. The signal occurring at the output 31 of the differentiator 27 is smoothed by means of a pair of capacitors 29 and 30. The amplification of the output signal is determined by the ratio of the resistors 32 and 33 with respect to the resistors 25 and 26. The output signal is proportional to the current between the working electrode 2 and the counter electrode 4.

It is of essential significance for the correct operation of the circuit that the impedance of the voltage transformer 21 be small in comparison to the impedance of the electrode system (counter electrode, working electrode, and reference electrode). The impedance transformers 17, 23 and 24 serve for the obtaining of the corresponding potentials in a high resistance manner. The measured value tapped at the output 31 can be processed further for the end point identification of the titration.

Figure 3:
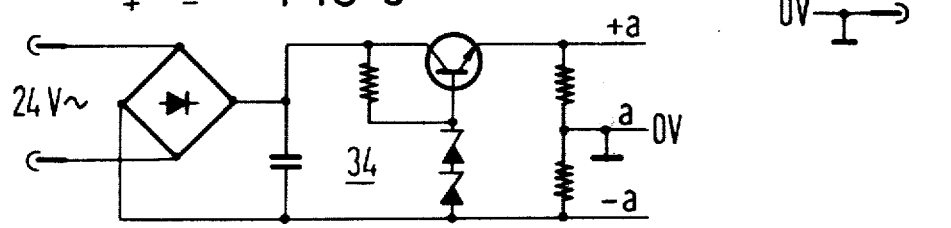
FIG. 3 is a schematic circuit diagram of a power supply for the measuring circuit and closed-loop control according to FIG. 2.

In order to achieve a complete electrical separation between the electrode measuring system and ground or, respectively, ground of the control, a separate current supply 34 is to be provided, as illustrated in FIG. 3. This circuit is known per se and is not the subject matter of the present invention. The terminals for the other devices of the circuit are indicated at 35 and lead to a central power supply of the electronics.

Although I have described my invention by reference to a particular illustrative embodiment thereof, many changes and modifications of the invention may become apparent without departing from the spirit and scope of the invention. I therefore intend to include within the patent warranted hereon all such changes and modifications as may reasonably and properly be included within the scope of my contribution to the art.

I claim:

1. A circuit arrangement for an amperometric titration for determining the end point, in which the current is measured between a working electrode and a counter electrode in a vessel in which the titration agent is introduced and the current is measured as a function of the total volume of the titration agent added in volume units, and in which a reference electrode is provided in the vessel, comprising:
   a closed-loop control connected to the working counter and reference electrodes, and including a reference value input;
   a reference value generator connected to said reference value input for generating a reference value voltage;
   an impedance transformer connected to said reference electrode as a high impedance transformer; and
   a summing integrator connected to said reference value generator and said impedance transformer to produce a deviation signal representing the difference between said reference and actual values.

2. The circuit arrangement of claim 1, wherein:
   said reference value generator comprises a voltage divider and a stabilizing Zener diode connected in circuit therewith.

3. The circuit arrangement of claim 1, comprising:
   a resistor connecting said summing integrator to said counter electrode.

4. The circuit arrangement of claim 1, wherein the impedance of said impedance transformer is small with respect to that of the electrode system.

5. The circuit arrangement of claim 1, comprising:
   a resistor connected to the output of said summing integrator;
   a differentiator; and
   means connecting the ends of said resistor to the inputs of said differentiator.

6. The circuit arrangement of claim 5, wherein said means comprises:
   a pair of other impedance transformers.

7. The circuit arrangement of claim 1, comprising:
   a current supply connected to said reference value input as said reference value generator, and connected to supply said summing integrator and said impedance transformer operating as an actual value generator.

8. The circuit arrangement of claim 1, comprising:
   means for interrupting the circuit between the working and counter electrodes.

* * * * *